United States Patent
Wang et al.

(10) Patent No.: US 7,598,359 B2
(45) Date of Patent: Oct. 6, 2009

(54) BIS (INDOLESTYRYL) COMPOUND AND HIGH DENSITY RECORDING MEDIA UTILIZING THE SAME

(75) Inventors: Shin-Shin Wang, Hsinchu (TW); Jong-Lieh Yang, Hsinchu (TW); Chii-Chang Lai, Taichung Hsien (TW); Hui-Ping Tsai, Hsinchu (TW); Wen-Ping Chu, Taichung (TW); Chien-Wen Chen, Pingtung County (TW); Chien-Liang Huang, Taoyuan County (TW); Wen-Yih Liao, Taichung (TW); Ming-Chia Lee, Taichung Hsien (TW)

(73) Assignee: Industrial Technology Research Institute, Hsinchu (TW)

( * ) Notice: Subject to any disclaimer, the term of this patent is extended or adjusted under 35 U.S.C. 154(b) by 292 days.

(21) Appl. No.: 11/216,084

(22) Filed: Sep. 1, 2005

(65) Prior Publication Data
US 2007/0003873 A1     Jan. 4, 2007

(30) Foreign Application Priority Data
Jun. 30, 2005   (TW) ............................... 94122125 A

(51) Int. Cl.
  C07D 403/06   (2006.01)
  C07D 401/14   (2006.01)
  B32B 3/02     (2006.01)
(52) U.S. Cl. .................. 534/702; 546/99; 546/198; 548/402; 548/427; 548/455; 428/64.4; 428/64.8; 430/270.19; 430/270.2; 430/270.21; 430/945
(58) Field of Classification Search ........... 534/702; 546/99, 198; 548/402, 427, 455; 428/64.4, 428/64.8; 430/270.19, 270.2, 270.21, 945
See application file for complete search history.

(56) References Cited

U.S. PATENT DOCUMENTS

| | | | |
|---|---|---|---|
| 6,761,952 B1 * | 7/2004 | Lee et al. | 428/64.1 |
| 6,815,031 B2 | 11/2004 | Huang et al. | |
| 7,014,981 B2 * | 3/2006 | Wang et al. | 430/270.19 |
| 7,390,549 B2 * | 6/2008 | Wang et al. | 428/64.1 |
| 2002/0028918 A1 * | 3/2002 | Kasada et al. | 534/693 |
| 2005/0064335 A1 * | 3/2005 | Wang et al. | 430/270.18 |
| 2006/0142590 A1 * | 6/2006 | Wang et al. | 548/416 |
| 2007/0059641 A1 * | 3/2007 | Li et al. | 430/270.19 |

FOREIGN PATENT DOCUMENTS

| | | | |
|---|---|---|---|
| EP | 1 130 063 A1 | | 9/2001 |
| EP | 1 156 084 A2 | | 11/2001 |
| EP | 1 170 339 A2 | | 1/2002 |
| JP | 59-159165 | * | 9/1984 |
| JP | 6-43585 | * | 2/1994 |
| JP | 6-102608 | * | 4/1994 |
| JP | 11-34489 A | | 2/1999 |

OTHER PUBLICATIONS

Mushkalo et al., Chemical Abstracts, 88:38936, 1978.*
Mushkalo et al., Chemical Abstracts, 111:173939, 1989.*
Cressman, Chemical Abstracts, 43:22204, 1949.*

* cited by examiner

Primary Examiner—Fiona T Powers
(74) Attorney, Agent, or Firm—Birch, Stewart, Kolasch & Birch, LLP

(57) ABSTRACT

A bis(indolestyryl) compound. The bis(indolestyryl) compound has formula (I):

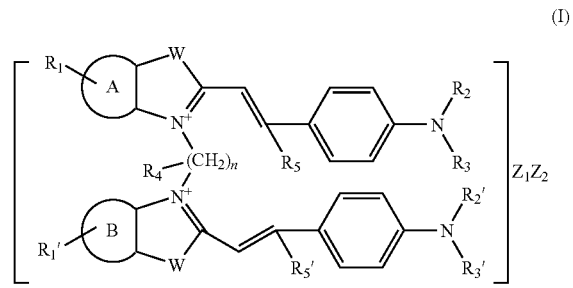

wherein A and B comprise benzene, naphthalene, or heterocyclic ring containing O, S, or N, $R_1$ and $R_1'$ are H, halogen, $C_{1-5}$ alkyl, nitro, ester, carboxyl, sulfo, sulfonamide, amide, sulfo ester, $C_{1-3}$ alkoxy, amino, alkylamino, cyano, $C_{1-6}$ alkylsulfonyl, or $C_{2-7}$ alkoxy carbonyl, $R_2$, $R_2'$, $R_3$, and $R_3'$ comprise H, $C_{1-6}$ alkyl, $C_{6-18}$ aryl, $C_{2-6}$ alkenyl, $C_{3-6}$ cycloalkenyl, or $C_{3-6}$ cycloalkyl, $R_4$ is H, $C_{1-5}$ alkyl, hydroxyl, halogen, or alkoxy, $R_5$ and $R_5'$ comprise H, halogen, $C_{1-5}$ alkyl, nitro, $C_{1-3}$ alkoxy, amino, cyano, $C_{1-6}$ alkylsulfonyl, or $C_{2-7}$ alkoxy carbonyl, W comprises oxygen, sulfur, selenium, —NR, or —C(CH$_3$)$_2$, n is 1~18 and $Z_1$ and $Z_2$ are different and comprise an anion or an anionic organometallic complex with +1 or +2 valence, wherein R bonded to nitrogen is $C_{1-4}$ alkyl.

23 Claims, 1 Drawing Sheet

BIS (INDOLESTYRYL) COMPOUND AND HIGH DENSITY RECORDING MEDIA UTILIZING THE SAME

BACKGROUND

The present invention relates to a bis(indolestyryl) compound, and more specifically to a bis(indolestyryl) compound used in a high density recording medium.

With advances in information and multimedia generation, computer, communication, and consumer (3C) electronic products with increased recording density and capacity, microminiaturization, and low cost are required to meet the flow of information. Currently, magnetic recording media have been replaced by high density optical recording media.

For optical recording media, improved recording density has been provided by, for example, reduction of wavelength of readout laser such as reduction from red light region to blue, or increase in the number aperture (NA). Another important research topic, however, is modification of organic dye structures in optical recording layers. Research has endeavored to develop optical dyes with high solubility, strong absorption in visible light region, photostability, thermal stability, or simple synthesis.

Dyes of CD-R are not suitable for use in high density recording media such as DVD-R due to their different laser wavelengths, CD-R having 780 nm and DVD-R 650 nm. Additionally, related organic dyes in recording layers lack photostability, thermal stability, and simple synthesis, resulting in shorter recording times and higher costs. Thus, development of organic dyes providing improved optical characteristics of high recording media is desirable.

SUMMARY

The invention provides a bis(indolestyryl) compound having formula (I):

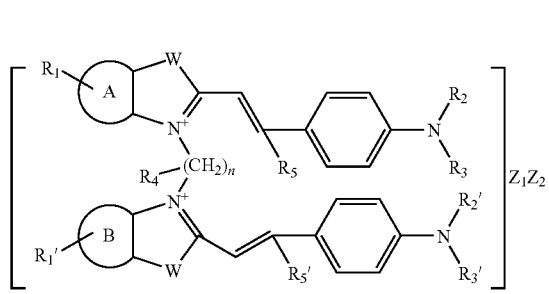

(I)

wherein A and B are the same or different and comprise benzene, naphthalene, or heterocyclic ring containing O, S, or N, $R_1$ and $R_1'$ are H, halogen atoms, $C_{1-5}$ alkyl, nitro, ester, carboxyl, sulfo, sulfonamide, amide, sulfo ester, $C_{1-3}$ alkoxy, amino, alkylamino, cyano, $C_{1-6}$ alkylsulfonyl, or $C_{2-7}$ alkoxy carbonyl, $R_2$, $R_2'$, $R_3$, and $R_3'$ are the same or different and comprise H, substituted or non-substituted $C_{1-6}$ straight chain or branched alkyl, substituted or non-substituted $C_{6-18}$ aryl, $C_{2-6}$ straight chain or branched alkenyl, $C_{3-6}$ cycloalkenyl, or substituted or non-substituted $C_{3-6}$ cycloalkyl, $R_4$ is H, $C_{1-5}$ alkyl, hydroxyl, halogen atoms, or alkoxy, $R_5$ and $R_5'$ are the same or different and comprise H, halogen atoms, $C_{1-5}$ alkyl, nitro, $C_{1-3}$ alkoxy, amino, cyano, $C_{1-6}$ alkylsulfonyl, or $C_{2-7}$ alkoxy carbonyl, W comprises oxygen, sulfur, selenium, —NR, or —C(CH$_3$)$_2$, n is 1~18, and $Z_1$ and $Z_2$ are different and comprise an anion or an anionic organometallic complex with +1 or +2 valence, wherein $R_2$ and $R_3$ or $R_2'$ and $R_3'$ are joined together or with a benzene to form a ring, and R bonded to nitrogen is $C_{1-4}$ alkyl.

The invention also provides a high density recording medium comprising a first substrate, a recording layer formed thereon comprising the disclosed bis(indolestyryl) compound, a reflective layer formed on the recording layer, and a second substrate formed on the reflective layer.

Further scope of the applicability of the present invention will become apparent from the detailed description given hereinafeter. However, it shouold understood that the detailed description and specific examples, while indicatiing preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the subsequent detailed description and the accompanying drawing, which are given by way of illustration only, and thus are not limitative of the present invention, and wherein.

DETAILED DESCRIPTION

Figure 1:
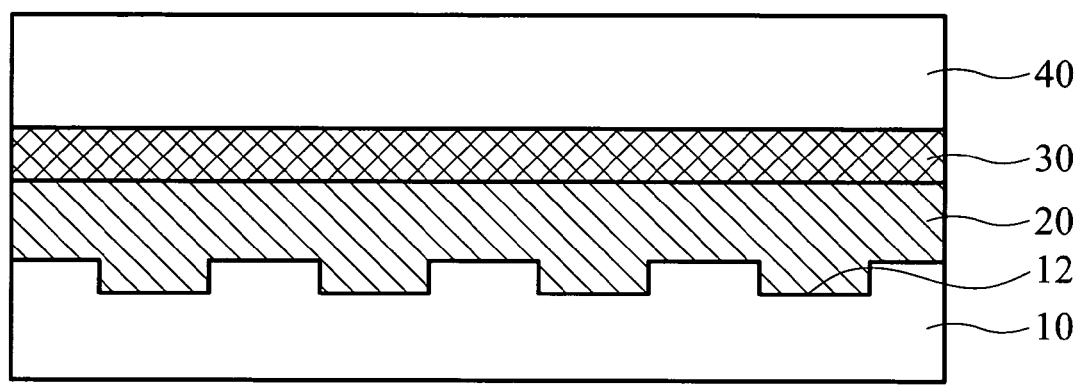
FIG. 1 is a cross section of a high density recording medium of the invention.

The invention provides a bis(indolestyryl) compound having formula (I):

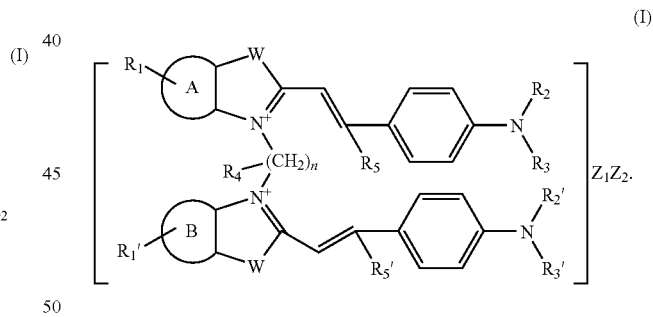

(I)

In formula (I), A and B are the same or different such as benzene, naphthalene, and heterocyclic ring containing O, S, or N, such as furan, pyrazine, pyrrole, pyrazole, pyridazine, pyridine, pyridone, pyrimidine, thiazole, thiophene, quinine, and isoquinine.

$R_1$ and $R_1'$ may comprise H, halogen atoms, $C_{1-5}$ alkyl, nitro, ester, carboxyl, sulfo, sulfonamide, amide, sulfo ester, $C_{1-3}$ alkoxy, amino, alkylamino, cyano, $C_{1-6}$ alkylsulfonyl, or $C_{2-7}$ alkoxy carbonyl.

$R_2$, $R_2'$, $R_3$, and $R_3'$ are the same or different such as H, substituted or non-substituted $C_{1-6}$ straight chain or branched alkyl, substituted or non-substituted $C_{6-18}$ aryl, $C_{2-6}$ straight chain or branched alkenyl, $C_{3-6}$ cycloalkenyl, or substituted and non-substituted $C_{3-6}$ cycloalkyl. $R_2$ and $R_3$ or $R_2'$ and $R_3'$ may be joined together or with a benzene to form a ring. Substituted groups in $R_2$, $R_2'$, $R_3$, and $R_3'$ may comprise H, oxygen, nitrogen, sulfur, halogen atoms, alkyl, alkyl halide, nitro, cyano, hydroxyl, carboxyl, ester, sulfo, sulfo ester, or sulfoamide.

$R_4$ may comprise H, $C_{1-5}$ alkyl, hydroxyl, halogen atoms, or $C_{1-5}$ alkoxy. $R_5$ and $R_5'$ are the same or different such as H, halogen atoms, $C_{1-5}$ alkyl, nitro, $C_{1-3}$ alkoxy, amino, cyano, $C_{1-6}$ alkylsulfonyl, and $C_{2-7}$ alkoxy carbonyl. W may comprise oxygen, sulfur, selenium, —NR, or —C(CH$_3$)$_2$, wherein R is $C_{1-4}$ alkyl. n is 1~18, and $Z_1$ and $Z_2$ are different and may comprise an anion or an anionic organometallic complex with −1 or −2 valence, such as halogen atoms, $ClO_4^-$, $BF_4^-$, $PF_6^-$, $BPh_4^-$, $SbF_6^-$, tetracyano p-quinodimethane (TCNQ$^-$), tetracyano ethylene (TCNE$^-$), benzene sulfonate, $Z_1$ and $Z_2$ have a weight ratio of about 1:99~99:1. The bis(indolestyryl) compound has an absorbing wavelength of about 400~700 nm, an absorbing coefficient ($\epsilon$) exceeding $10^5$, and solubility exceeding 2% in organic solvent such as $C_{1-6}$ alcohol, $C_{1-6}$ ketone, $C_{1-8}$ ether, halide, and amide.

The bis(indolestyryl) compounds provided by the invention comprise

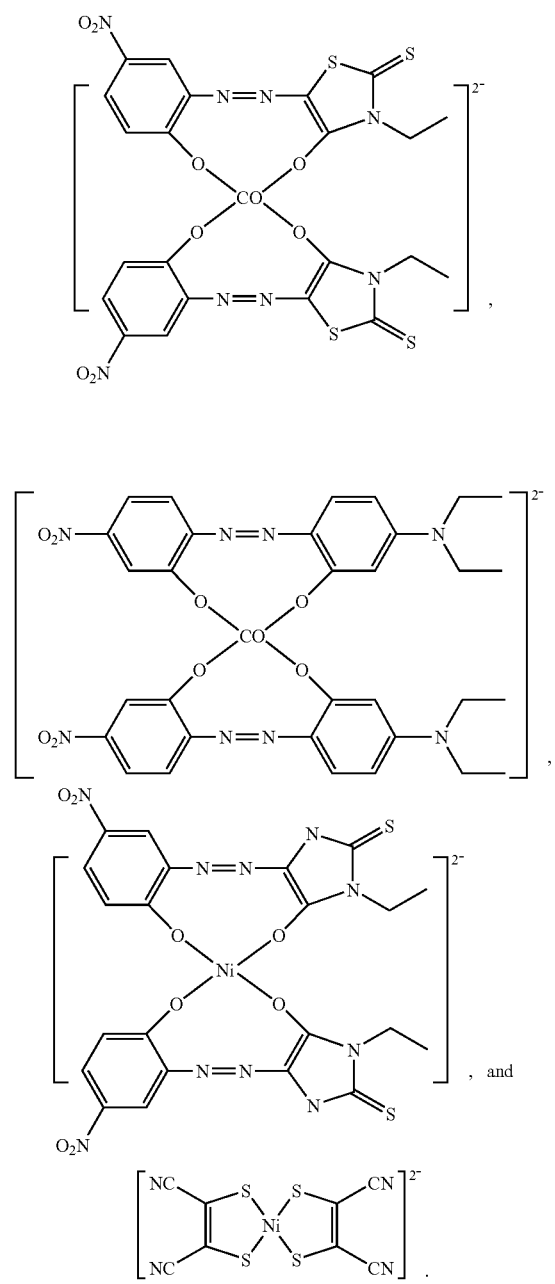

, and

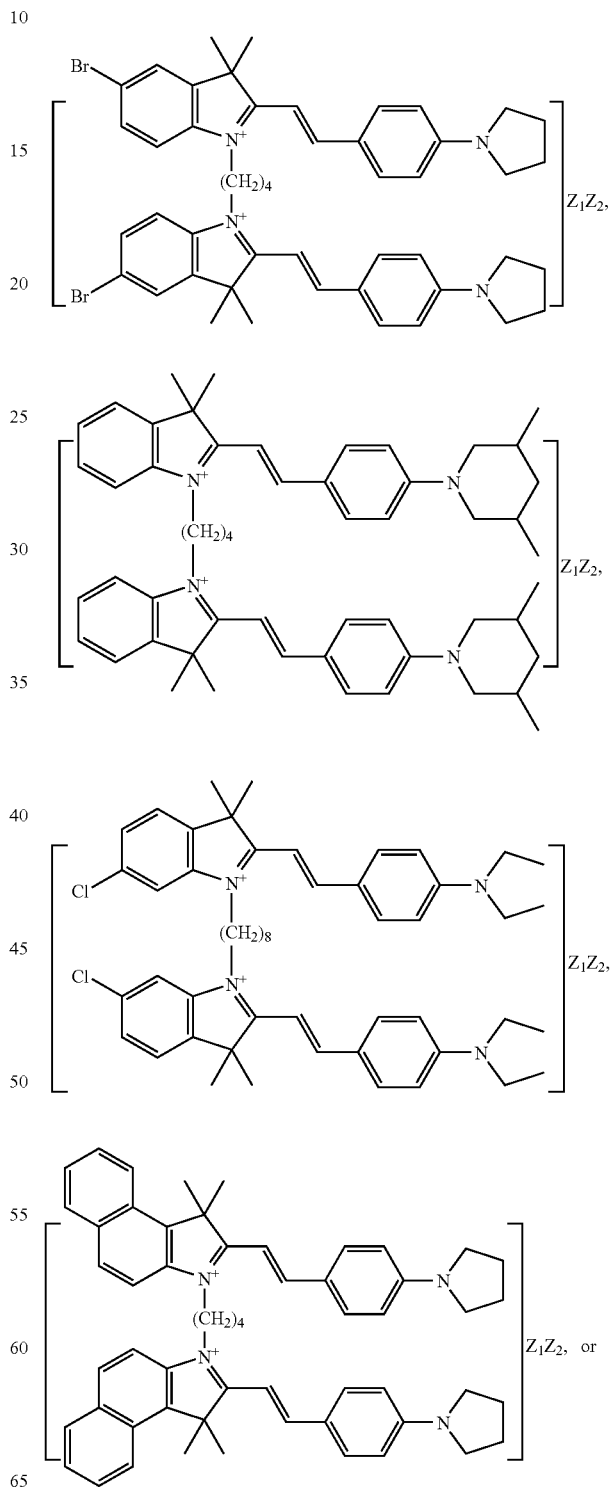

, or

-continued

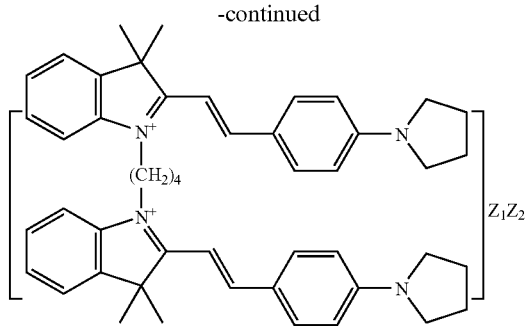

wherein $Z_1$ and $Z_2$ are different and may comprise an anion or an anionic organometallic complex with +1 or +2 valence.

The compound of formula (I) is prepared as follows.

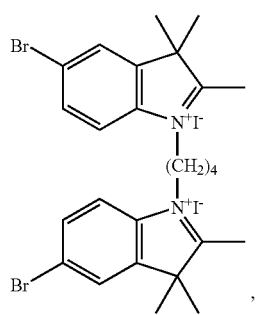

First, a bis-compound of such as

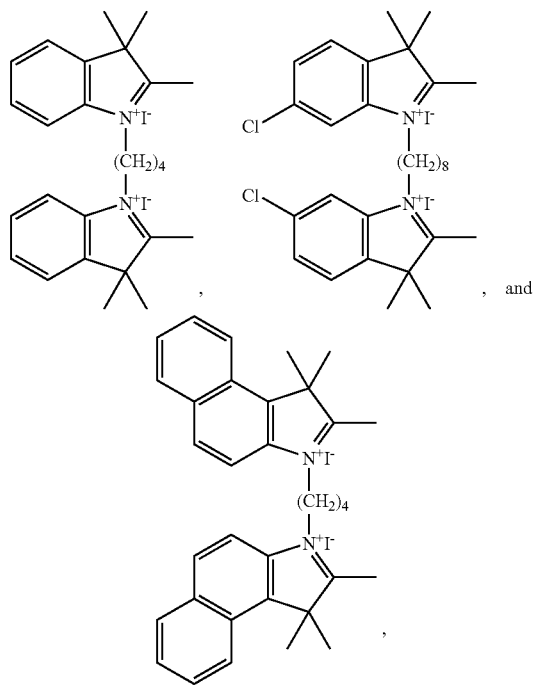

solvent such as ethanol or methanol, and benzaldehyde such as 4-diethylaminobenzaldehyde, 4-(1-pyrrolidino)benzaldehyde, and 4-(1-(3,5-dimethylpiperidino)) benzaldehyde, are added to a flask and reacted for 20~24 hours. A bis(indolestyryl) compound is prepared after extracting solvent. The bis(indolestyryl) compound, solvent such as methanol or ethanol, a metal salt, and an anionic organometallic complex are added to a flask and reacted. The metal salt may comprise Li, Na, or K salt such as $NaSbF_6$, $NaClO_4$, and $NaPF_6$. The anionic organometallic

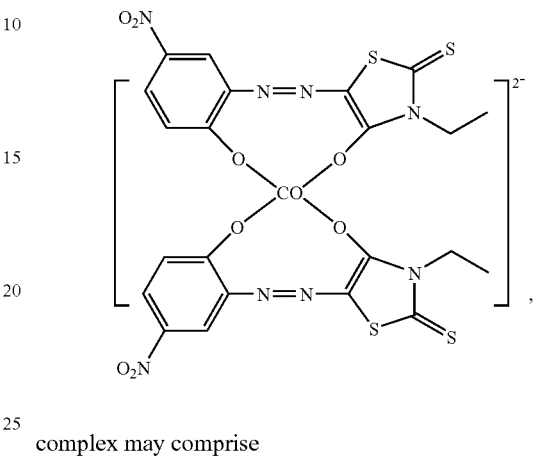

complex may comprise

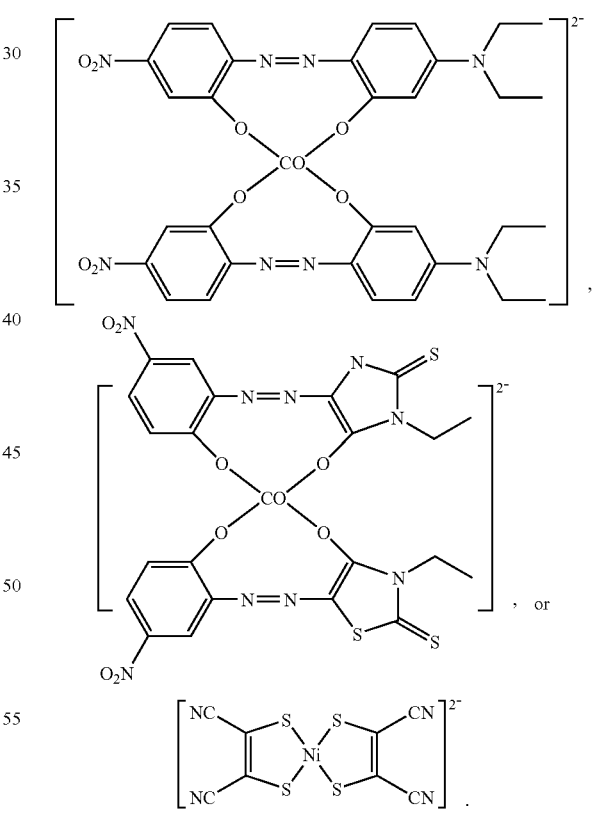

After cooling to room temperature and filtration, a bis(indolestyryl) compound is produced.

The invention also provides a high density recording medium comprising a first substrate, a recording layer formed thereon comprising the disclosed bis(indolestyryl) compound, a reflective layer formed on the recording layer, and a second substrate formed on the reflective layer.

The first and second substrates are transparent substrates and comprise polyester, polycarbonate, or polyolefin. The recording layer has a thickness of about 50~300 nm and comprises bis(indolestyryl), cyanine dye or azo metal chelate compounds. The bis(indolestyryl) compound and cyanine dye or azo metal chelate compounds have a weight ratio of about 1:99~99.9:0.1. The reflective layer may comprise Au, Ag, Al, Cu, Cr, or alloys thereof.

The high density recording medium has a reflectance of about 40~60%, preferably 45%, a jitter of about 8~10, and a modulation of about 0.6~0.8. The high density recording medium may comprise a Digital Versatile Disk-Recordable (DVD-R).

A method of fabricating a high density recording medium is further provided. A first substrate having trenches is provided and a solution containing a bis(indolestyryl) compound and solvent is prepared simultaneously. The solvent may comprise $C_{1-6}$ alcohol, $C_{1-6}$ ketone, $C_{1-8}$ ether, dibutyl ether (DBE), halide, or amide. The $C_{1-6}$ alcohol comprises methanol, ethanol, isopropanol, diacetone alcohol (DAA), 2,2,3,3-tetrafluoropropanol (TFP), trichloroethanol, 2-chloroethanol, octafluoropentanol, or hexafluorobutanol. The $C_{1-6}$ ketone comprises acetone, methyl isobutyl ketone (MIBK), methyl ethyl ketone (MEK), or 3-hydroxy-3-methyl-2-butanone. The halide comprises chloroform, dichloromethane, or 1-chlorobutane. The amide comprises dimethyl formamide (DMF), dimethyl acetamide (DMA), or methyl cyclohexane (MCH). The solution is then coated on the first substrate and dried to form a recording layer, utilizing spin coating, vacuum deposition, spray coating, immersion coating, stick coating, fluid coating, printing coating, or tape coating, preferably spin-coating. Next, a reflective layer is evaporated on the recording layer. Finally, a second substrate is bonded to the reflective layer to form a high density recording medium. A protection layer may be coated on the reflective layer before the second substrate is bonded.

EXAMPLES

Example 1

Preparation of Compound 1

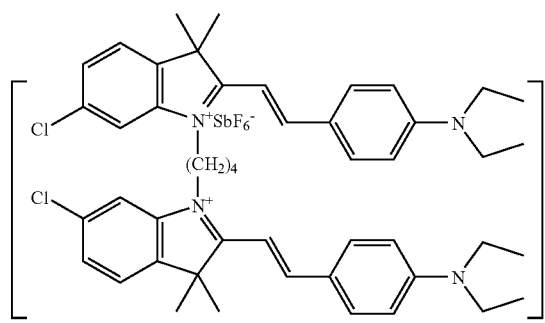

-continued

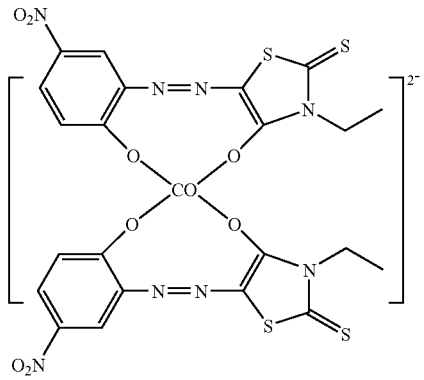

2.0 g

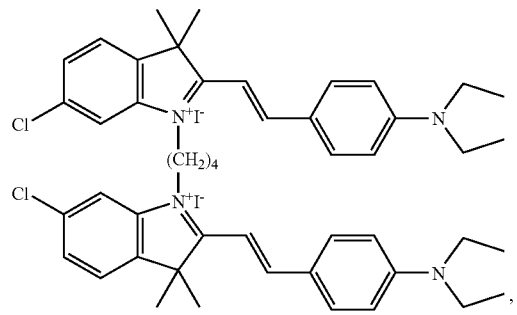

0.95 g $NaSbF_6$, 1.1 g

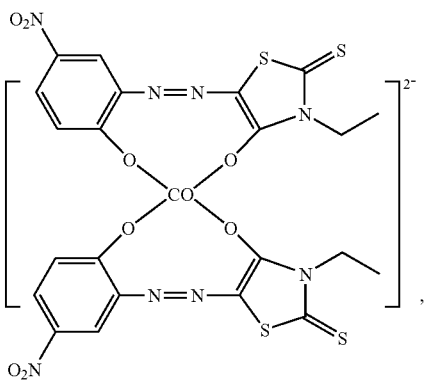

and 30 ml methanol were added to a 50 ml flask (NaSbF$_6$ and

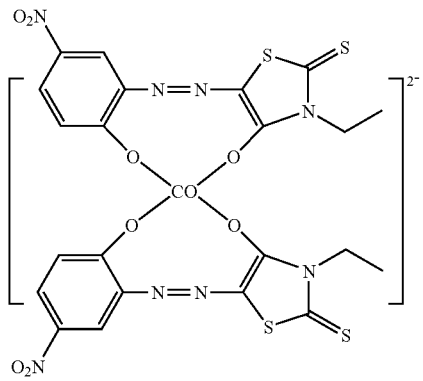

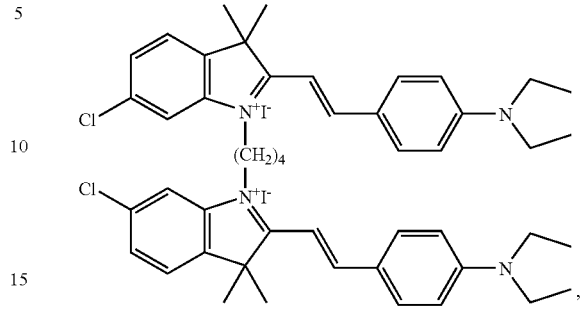

had a weight ratio of 46:54) with thermal reflux overnight. After cooling to room temperature and filtration, 1.14 g green compound 1 was prepared with yield of 42.7% and purity of 100%. Compound 1 had a maximum absorbing wavelength of 566 nm in methanol and $\epsilon=2.2*10^5$.

Example 2

Preparation of Compound 2

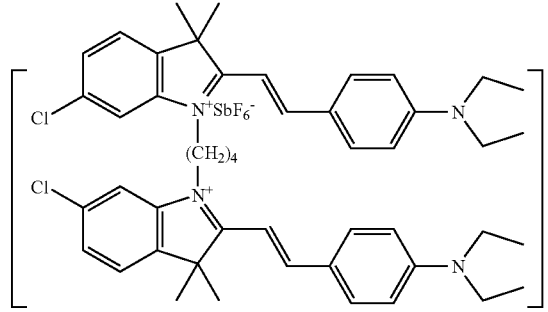

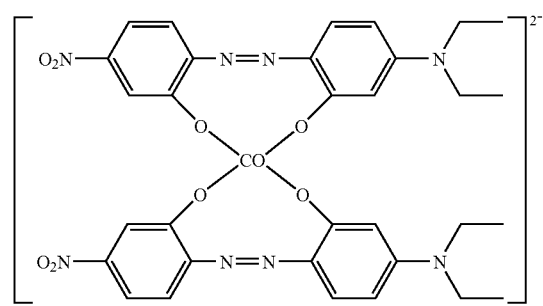

1.5 g 0.78 g NaSbF$_6$, 0.4 g

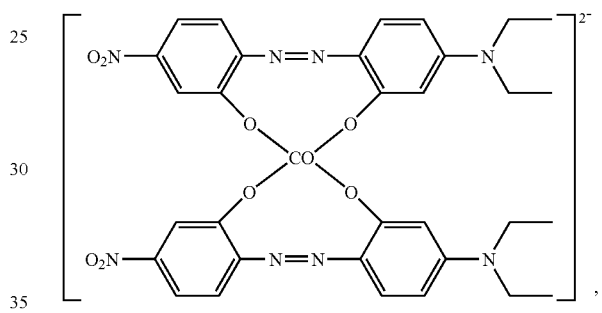

and 22 ml methanol were added to a 50 ml flask (NaSbF$_6$ and

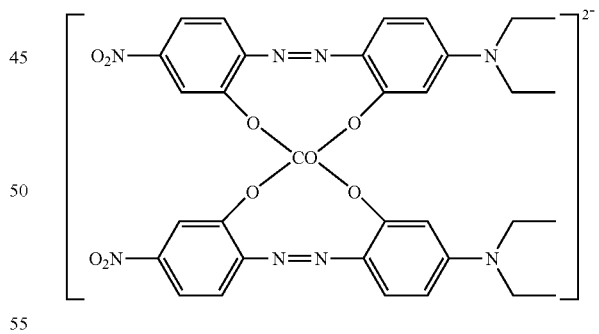

had a weight ratio of 66:34) with thermal reflux overnight. After cooling to room temperature and filtration, 1.55 g green color compound 2 was prepared with yield of 78.2% and purity of 100%. Compound 2 had a maximum absorbing wavelength of 565 nm in methanol and $\epsilon=1.56*10^5$.

Five bis(indolestyryl) compounds (compound 1~5) were prepared, with various structures and weight ratios of anionic groups ($Z_1$ and $Z_2$) and maximum absorbing wavelengths (nm) as shown in Table 1.

TABLE 1

| bis(indolestyryl) | $Z_1$ | $Z_2$ | $Z_1:Z_2$ (%) | $\lambda_{max}$ (nm) |
|---|---|---|---|---|
| 1 | $SbF_6^-$ | | 46:54 | 566 |
| 2 | $SbF_6^-$ | | 66:34 | 565 |
| 3 | $ClO_4^-$ | | 24:76 | 563 |
| 4 | $SbF_6^-$ | | 34:66 | 563 |

TABLE 1-continued

| bis(indolestyryl) | $Z_1$ | $Z_2$ | $Z_1:Z_2$ (%) | $\lambda_{max}$ (nm) |
|---|---|---|---|---|
| 5 [bis-indolestyryl pyrrolidine structure] | $SbF_6^-$ | [Ni(mnt)$_2$]$^{2-}$ structure | 46:54 | 558 |

The bis(indolestyryl) compounds provided by the invention comprise

, or

-continued

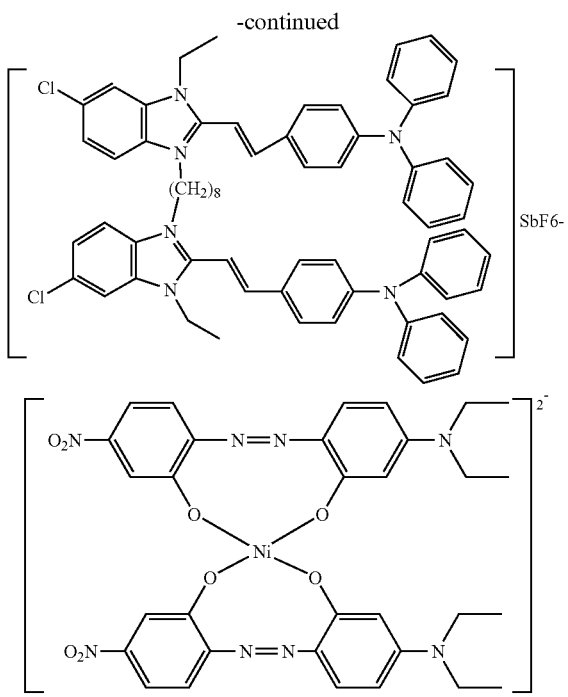

Example 3

Fabrication of High Density Recording Medium

Referring to FIG. 1, a method of fabricating a high density recording medium is disclosed according to the following example, in which a polycarbonate first substrate 10 at a diameter of 120 mm and a thickness of 1.2 mm having trenches 12 at a depth of 130 nm and a width of 300 nm was provided. A solution (1.7 wt %) containing a compound 2 and 2,2,3,3-tetrafluoropropanol (TFP) was prepared simultaneously. Next, the solution was coated on the first substrate 10 by spin coating and dried at 80° C. for 5 min to form a recording layer 20. An Ag layer was then sputtered on the recording layer 20 to form a reflective layer 30 at a thickness of 200 nm. Finally, a second substrate 40 was bonded to the reflective layer 30 to form a high density recording medium. A UV resin was coated on the reflective layer 30 to form a protective layer of about 10 μm (not shown) before the second substrate 40 was bonded.

Reflectance, jitter, and modulation of high density recording media are shown in Table 2.

TABLE 2

|  | Reflectance (%) | Jitter | Modulation |
|---|---|---|---|
| High density recording medium | 45.3 | 9 | 0.682 |

The results indicate that the high density recording media with modified recording layers of the invention provides better photoelectrical performance. Reflectance, jitter, and modulation of related products are 45%, 8.0, and 0.6, respectively. Additionally, these media also provide high recording sensitivity and high carrier-to-noise ratio (CNR).

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A bis(indolestyryl) compound of the formula (I):

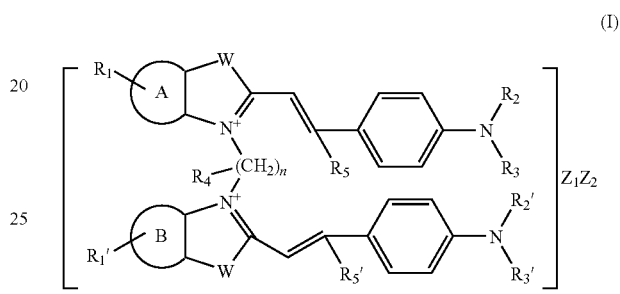

(I)

wherein A and B are the same or different and are benzene, pyridone, or heterocyclic ring containing O, S, or N, $R_1$ and $R_1'$ are H, halogen, $C_{1-5}$ alkyl, nitro, ester, carboxyl, sulfo, sulfonamide, amide, sulfo ester, $C_{1-3}$ alkoxy, amino, $C_{1-5}$ alkylamino, cyano, $C_{1-6}$ alkylsulfonyl, or $C_{2-7}$ alkoxy carbonyl, $R_2$, $R_2'$, $R_3$, and $R_3'$ are the same or different and are H, substituted or non-substituted $C_{1-6}$ straight chain or branched alkyl, substituted or non-substituted $C_{6-18}$ aryl, $C_{2-6}$ straight chain or branched alkenyl, $C_{3-6}$ cycloalkenyl, or substituted or non-substituted $C_{3-6}$ cycloalkyl, $R_4$ is H, $C_{1-5}$ alkyl, hydroxyl, halogen, or $C_{1-5}$ alkoxy, $R_5$ and $R_5'$ are the same or different and are H, halogen, $C_{1-5}$ alkyl, nitro, $C_{1-3}$ alkoxy, amino, cyano, $C_{1-6}$ alkylsulfonyl, or $C_{2-7}$ alkoxy carbonyl, W is oxygen, sulfur, selenium, —NR, or —C(CH$_3$)$_2$, n is 1~18, and $Z_1$ and $Z_2$ are different and are an anion or an anionic organometallic complex with −1 or −2 valence, wherein $R_2$ and $R_3$ or $R_2'$ and $R_3'$ are joined together or with a benzene to form a ring, and R bonded to nitrogen is $C_{1-4}$ alkyl.

2. The bis(indolestyryl) compound as claimed in claim 1, wherein A and B are furan, pyrazine, pyrrole, pyrazole, pyridazine, pyridine, pyridone, pyrimidine, thiazole or thiophene.

3. The bis(indolestyryl) compound as claimed in claim 1, wherein said substitutes of $R_2$, $R_2'$, $R_3$, and $R_3'$, when present are alkyl, alkyl halide, ester, sulfo, sulfo ester, or sulfoamide.

4. The bis(indolestyryl) compound as claimed in claim 1, wherein $Z_1$ and $Z_2$ are halogen, $ClO_4^-$, $BF_4^-$, $PF_6^-$, $BPh_4^-$, $SbF_6^-$, tetracyano p-quinodimethane (TCNQ$^-$), tetracyano ethylene (TCNE$^-$), or benzene sulfonate.

5. The bis(indolestyryl) compound as claimed in claim 1, wherein $Z_1$ and $Z_2$ are

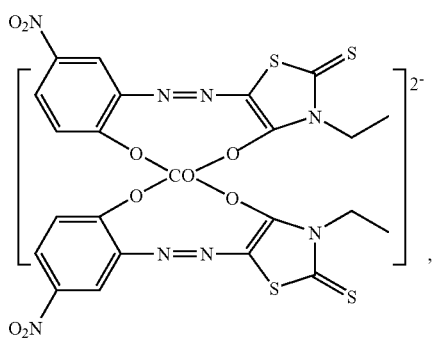

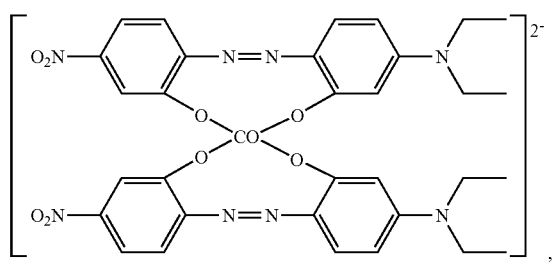

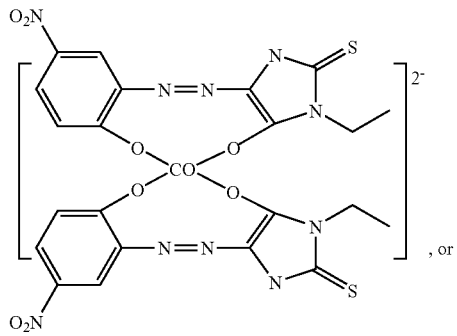

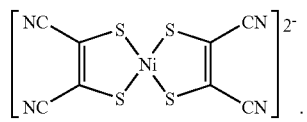

6. The bis(indolestyryl) compound as claimed in claim 1, wherein the bis(indolestyryl) compound is

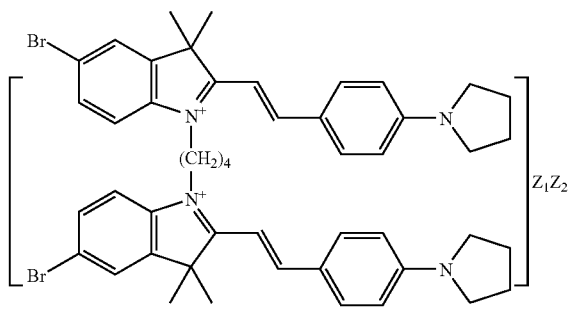

wherein $Z_1$ and $Z_2$ are different and are an anion or an anionic organometallic complex with −1 or −2 valence.

7. A bis(indolestyryl) compound, which is

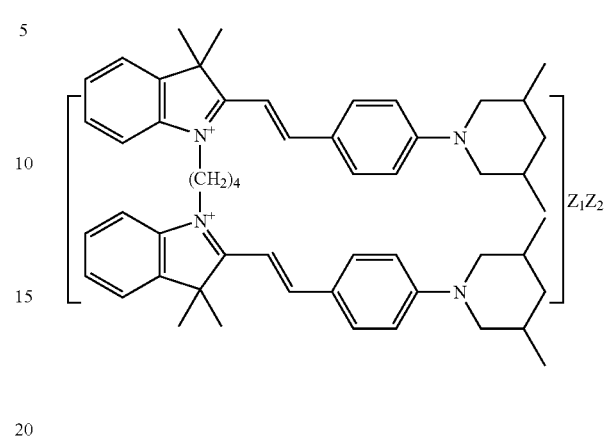

wherein $Z_1$ and $Z_2$ are different and are an anion or an anionic organometallic complex with −1 or −2 valence.

8. The bis(indolestyryl) compound as claimed in claim 1, wherein the bis(indolestyryl) compound is

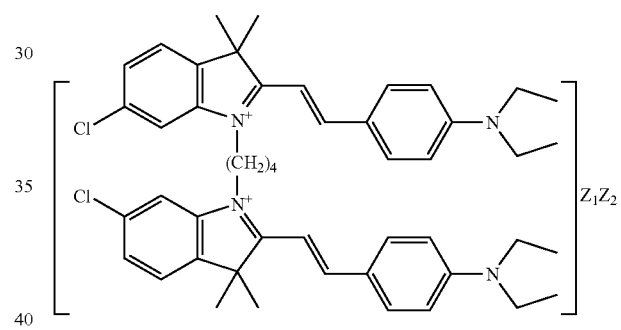

wherein $Z_1$ and $Z_2$ are different and are an anion or an anionic organometallic complex with −1 or −2 valence.

9. The bis(indolestyryl) compound as claimed in claim 1, wherein the bis(indolestyryl) compound is

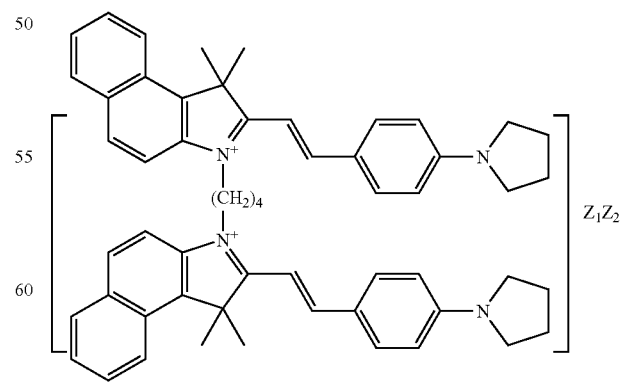

wherein $Z_1$ and $Z_2$ are different and are an anion or an anionic organometallic complex with −1 or −2 valence.

10. The bis(indolestyryl) compound as claimed in claim 1, wherein the bis(indolestyryl) compound is

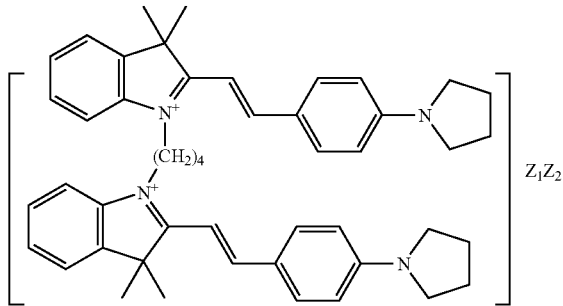

wherein $Z_1$ and $Z_2$ are different and are an anion or an anionic organometallic complex with −1 or −2 valence.

11. The bis(indolestyryl) compound as claimed in claim 1, wherein $Z_1$ and $Z_2$ have a weight ratio of about 1:99~99:1.

12. The bis(indolestyryl) compound as claimed in claim 1, wherein the bis(indolestyryl) compound has an absorbing wavelength of about 400~700 nm.

13. The bis(indolestyryl) compound as claimed in claim 1, wherein the bis(indolestyryl) compound has an absorbing coefficient ($\epsilon$) exceeding $10^5$.

14. The bis(indolestyryl) compound as claimed in claim 1, wherein the bis(indolestyryl) compound has solubility exceeding 2% in organic solvent.

15. The bis(indolestyryl) compound as claimed in claim 14, wherein the organic solvent is $C_{1-6}$ alcohol, $C_{1-6}$ ketone, $C_{1-8}$ ether, halide, or amide.

16. A high density recording medium, comprising:
a first substrate;
a recording layer formed on the first substrate comprising a bis(indolestyryl) compound as claimed in claim 1;
a reflective layer formed on the recording layer; and
a second substrate formed on the reflective layer.

17. The high density recording medium as claimed in claim 16, wherein the first substrate is a transparent substrate comprising trenches.

18. The high density recording medium as claimed in claim 16, wherein the first and second substrates are polyester, polycarbonate, or polyolefin.

19. The high density recording medium as claimed in claim 16, wherein the recording layer is cyanine dye or azo metal chelate compounds.

20. The high density recording medium as claimed in claim 19, wherein the bis(indolestyryl) compound and cyanine dye or azo metal chelate compounds have a weight ratio of about 1:99~99.9:0.1.

21. The high density recording medium as claimed in claim 16, wherein the reflective layer is Au, Ag, Al, Cu, Cr, or alloys thereof.

22. The high density recording medium as claimed in claim 16, wherein the high density recording medium has a reflectance exceeding 45%, a jitter of about 8-10, and a modulation of about 0.6~0.9.

23. The high density recording medium as claimed in claim 16, wherein the high density recording medium is a High Density Digital Versatile Disk-Recordable (DVD-R).

* * * * *